US011134628B2

(12) United States Patent
Brugmans et al.

(10) Patent No.: US 11,134,628 B2
(45) Date of Patent: Oct. 5, 2021

(54) **METHODS AND COMPOSITIONS FOR *PERONOSPORA* RESISTANCE IN SPINACH**

(71) Applicant: SEMINIS VEGETABLE SEEDS, INC., St. Louis, MO (US)

(72) Inventors: Bart Willem Brugmans, Beek en Donk (NL); Eduardo López Fernandez, Rotterdam (NL); Rosa I. Weber, Wageningen (NL)

(73) Assignee: SEMINIS VEGETABLE SEEDS, INC, St. Louis, MO (US)

( * ) Notice: Subject to any disclaimer, the term of this patent is extended or adjusted under 35 U.S.C. 154(b) by 0 days.

(21) Appl. No.: 16/680,292

(22) Filed: Nov. 11, 2019

(65) Prior Publication Data

US 2020/0170208 A1 Jun. 4, 2020

Related U.S. Application Data

(63) Continuation of application No. 15/349,677, filed on Nov. 11, 2016, now Pat. No. 10,575,483, which is a continuation of application No. 14/509,215, filed on Oct. 8, 2014, now Pat. No. 10,039,258.

(60) Provisional application No. 61/899,780, filed on Nov. 4, 2013, provisional application No. 61/888,501, filed on Oct. 8, 2013.

(51) Int. Cl.
*A01H 6/02* (2018.01)
*A01H 5/12* (2018.01)
*A01H 1/04* (2006.01)
*A01H 1/00* (2006.01)

(52) U.S. Cl.
CPC ............. *A01H 6/028* (2018.05); *A01H 1/04* (2013.01); *A01H 1/1245* (2021.01); *A01H 5/12* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 4,900,659 | A | 2/1990 | Lo |
| 7,935,864 | B2 | 5/2011 | Baerneds |
| 7,935,865 | B2 | 5/2011 | Baerends |
| 7,935,866 | B2 | 5/2011 | Baerends |
| 7,935,867 | B2 | 5/2011 | Baerends |
| 7,935,868 | B2 | 5/2011 | Baerends |
| 7,939,717 | B2 | 5/2011 | Baerends |
| 7,939,718 | B2 | 5/2011 | Baerends |
| 7,939,719 | B2 | 5/2011 | Baerends |
| 7,939,720 | B2 | 5/2011 | Baerends |
| 8,008,548 | B2 | 8/2011 | DeWit et al. |
| 8,354,570 | B2 | 1/2013 | Van Den Ackerveken et al. |
| 8,563,807 | B2 | 10/2013 | Dijkstra |
| 8,735,659 | B2 | 5/2014 | Baerends |
| 8,742,207 | B2 | 6/2014 | Van Damme et al. |
| 8,772,573 | B2 | 7/2014 | Baerends |
| 8,772,574 | B2 | 7/2014 | Baerends |
| 9,086,083 | B2 | 7/2015 | Hooper et al. |
| 9,265,275 | B2 | 2/2016 | den Braber |
| 9,295,219 | B2 | 3/2016 | den Braber |
| 9,332,724 | B2 | 5/2016 | den Braber |
| 9,332,775 | B2 | 5/2016 | den Braber |
| 9,402,363 | B1 | 8/2016 | Feitsma et al. |
| 9,456,578 | B2 | 10/2016 | den Braber |
| 9,485,954 | B2 | 11/2016 | den Braber |
| 9,609,839 | B2 | 4/2017 | Baerends |
| 9,615,531 | B2 | 4/2017 | Den Braber |
| 9,615,532 | B2 | 4/2017 | Den Braber |
| 10,039,258 | B2 * | 8/2018 | Brugmans et al. .... A01H 6/028 |
| 10,226,016 | B2 | 3/2019 | Feitsma et al. |
| 10,575,483 | B2 * | 3/2020 | Brugmans et al. ...... A01H 1/04 |
| 2006/0134663 | A1 | 6/2006 | Harkin et al. |
| 2007/0016976 | A1 | 1/2007 | Katagiri et al. |
| 2013/0036516 | A1 | 2/2013 | Hatzfeld et al. |
| 2013/0198884 | A1 | 8/2013 | Dijkstra |
| 2013/0243931 | A1 | 9/2013 | Baerends |
| 2014/0065287 | A1 * | 3/2014 | den Braber et al. ..... A01H 5/12 426/615 |
| 2015/0240256 | A1 | 8/2015 | Brugmans et al. |
| 2016/0177330 | A1 * | 6/2016 | Dijkstra ............. C12N 15/8282 800/265 |

(Continued)

FOREIGN PATENT DOCUMENTS

| AU | 2014203678 | 1/2015 |
| EP | 2586294 | 5/2013 |
| JP | S56106567 | 8/1981 |
| JP | S62179357 | 8/1987 |

(Continued)

OTHER PUBLICATIONS

Hallavant & Ruas(2014) Veget Hist Archaeobot 23(2): 153-65.*
Correll et al. (2011) Eur J Plant Pathol 129:193-205.*
Kik (2011) Spinach Conference, Amsterdam, p. 26.*
Irish et al. (2008) Phytopath 98(8):894-900.*
Yang et al. (2016) PloS One 11 (5):e015270.*
Irish et al. (2007) Plant Dis 91:1392-96.*
She et al. (2018) Theor Appl Genet 131 :2529-41.*
Amundadottir et al., "A common variant associated with prostate cancer in European and African populations," *Nature Genetics* 38(6):652-658, 2006.

(Continued)

*Primary Examiner* — Russell T Boggs
(74) *Attorney, Agent, or Firm* — Dentons US LLP; Alissa Eagle

(57) ABSTRACT

The present disclosure provides for unique spinach plants with broad-spectrum resistance to downy mildew and their progeny. Such plants may comprise an introgressed QTL associated with the broad-spectrum resistance to downy mildew. In certain aspects, compositions, including distinct polymorphic molecular markers, and methods for producing, using, identifying, selecting, and the like of plants or germplasm with resistance to downy mildew are provided.

5 Claims, 2 Drawing Sheets

Specification includes a Sequence Listing.

(56) References Cited

U.S. PATENT DOCUMENTS

| | | | | |
|---|---|---|---|---|
| 2017/0327839 | A1* | 11/2017 | Feitsma et al. | A01H 5/12 |
| 2019/0127753 | A1 | 5/2019 | Kock et al. | |

FOREIGN PATENT DOCUMENTS

| | | |
|---|---|---|
| JP | 2008-502335 | 1/2008 |
| JP | 2008-141994 | 6/2008 |
| JP | 2009-513152 | 4/2009 |
| KR | 1211741 | 12/2012 |
| WO | WO 2005/124108 | 12/2005 |
| WO | WO 2007/051626 | 5/2007 |
| WO | WO 2013/064436 A1 | 5/2013 |
| WO | WO 2015/036378 | 3/2015 |
| WO | WO 2018/059651 A1 * | 4/2018 |

OTHER PUBLICATIONS

Bentley, et al., "Generation of an open pollinated near-isogenic spinach line with homozygous resistance to the down mildew pathogen," *Pytopathology*, 96(6):S12, APS Annual Meeting, 2006 (abstract).

Brandenberger et al., "Evaluation of Spinach Germplasm for Resistance to a New Race (Race 4) of *Peronospora farinosa* f. sp. *spinaciae*," *HortScience*, 27(20):1118-1119, 1992.

Brenner, "The US Spinach Germplasm Collection," presented at the T.E. Morelock International Spinach Conference, Fayetteville, AR, 2009 (abstract).

Correll et al., "Spinach: better management of downy mildew and white rust through genomics," *Eur J Plant Pathol* 129:193-205, 2011.

Correll et al., "Quantitative resistance to race 6 of the down mildew pathogen (*Peronosporia farinosa* f. sp. *spinciae*)," *Pytopathology*, 90(6Supp.):S16, 2000 . . . .

Eenink, "Linkage in spinacia-oleracea of two race specific genes for resistance to downy mildew *Peronospora-farinosa*-f-sp *spinaciae*," *Euphytica* 25(3):713-715, 1976.

Eenink, et al., Resistance in spinach (*Spinacia oleracea* L.) to false mildew (*Peronospora spinaciae* Laub.), *Zaadbelangen* 39(4):101-103, 1976.

European Search Report for EP15156928, dated Jul. 20, 2015.

Examination Report dated Jul. 13, 2015 in New Zealand Application No. 630710.

Examination Report dated Sep. 26, 2014 in New Zealand Application No. 630710.

Femie et al., "Natural genetic variation for improving crop quality," *Curr Opin Plant Biol* 9:196-202, 2006.

GenBank Accession No. AE004969.1, submitted Mar. 10, 2003.

Google "corresponding" ; define "Corresponding" 2018.

Hallavant et al., The first archaeobotanical evidence of *Spinacia oleraceo* L. (spinach) in late $12^{th}$-mid $13^{th}$ century AD France *Veget Hist Archaeobot* 23(2): 153-65; 2014.

Handke et al., "Detection of a linkage of the four dominant mildew resistance genes "M1M2M3M4" in spinach from the wildtype *Spinacia turkestanica*," *Garetnbauwissenschaft* 65(2):73-78, 2000 (English abstract).

International Search Report and Written Opinion for PCT Application No. PCT/US14/59610, dated Feb. 3, 2015.

Irish et al., "Characterization of a resistance locus (Pfs-1) to the spinach downy mildew pathogen (*Peronospora farinosa* f. sp *spinaciae*) and development of a molecular marker linked to Pfs-1," *Phytopathology* 98(8):894-900, 2008.

Irish et al., Molecular characterization of spinach germplasm and a marker linked to downy mildew resistance using AFLPs, *Phytopathology* 94(6):S44, 2004 (abstract).

Irish, et al., "Three new races of the spinach downy mildew pathogen identified by a modified set of spinach differentials," *Plant Disease*, 91(11):1392-1396, 2007.

Japanese Office Action regarding Japan Application No. JP2016-521258. dated Jul. 10, 2019.

Khattak et al., A genetic linkage map of Spinacia oleracea and localization of a sex determination locus, *Euphytica* 148:311-318, 2006.

Kik et al., "Spinach, Armenia and Azerbaijan, 2011" p. 26, Retrieved on Dec. 5, 2018. Available at <https://missions.cgn.wur.nl/NTC/NTC.htm>.

Kik et al., "The CGN Spinach Collection: Overview and Recent Collecting Expeditions," available at <spinach.uark.edu/Session%2011%PDFs/Chirs%20Kik.pdf>, 2011.

Lo et al., "Breast cancer risk associated with genotypic polymorphism of the mitosis-regulating gene Aurora-A/STK15/BTAK," *Int. J. Cancer* 115:276-283, 2005.

Mou et al., "Screening for resistance to leaf spot diseases of spinach," *HortScience*, 43(6):1706-1710, 2008.

Mou, "Leafminer resistance in spinach," *HortScience* 43(6):1716-1719, 2008.

Notice of Allowance and Fee(s) Due regarding U.S. Appl. No. 14/509,215, dated Mar. 30, 2018.

Official Gazette of the Community Plant Variety Office; Issue #6; accessed from www.cpvo.europa.eu; European Union Publications Office, 2013.

Polesskaya et al.," Allele C-Specific Methylation of the 5-HT2A Receptor Gene: Evidence for Correlation With Its Expression and Expression of DNA Methylase DNMT1," *Journal of Neuroscience Research* 83:362-373, 2006.

Response to Final Office Action regarding U.S. Appl. No. 14/509,215, dated Jan. 8, 2018.

Sadikhova, "Research and development of the vegetable system in Azerbaijan," In Increasing market-oriented vegetable production in Central Asia and the caucasus through collaborative research and development, pp. 29-35, 2006.

Smith, "Embryo culture of a tomato species hybrid," *Proc Am Soc Hort Sci*, 44:413-16, 1944.

Spinach varieties for industry crops, available at <http://www.rijkzwaan.com/wps/wcm/connect/rz+corporate/rijk+zwaan/products_and_services/products/industry/industry_crops+english/spinach>, accessed on Aug. 20, 2015.

Stam, "Construction of integrated genetic linkage maps by means of a new computer package: JoinMap," *Plant J* 3:739-844, 1993.

Tettelin et al., "Complete Genome Sequence of Neisseria meningitidis Serogroup B Strain MC58," *Science* 287:1809-1815, 2000.

USPTO: Final Office Action regarding U.S. Appl. No. 14/509,215, dated Nov. 16, 2017.

USPTO: Non-Final Office Action regarding U.S. Appl. No. 14/509,215, dated Jul. 13, 2017.

Xu et al., "Draft genome of spinach and transcriptome diversity of 120 Spinacia accessions," *Nature Communications* 8:15278, DOI:10.1038/ncomms15275, 2017.

Yang et al., "Initial fine mapping of the spinach downy mildew resistance locus RPFI," University of Arkansas, 2013, 102 pages.

Feng et al., "Identification of New Races and Deviating Strains of the Spinach Downy Mildew Pathogen *Peronospora farinosa* f. sp. *spinaciae*", Plant Disease, 98(1):145-152, 2014.

Arumuganathan et al., "Nuclear DNA Content of Some Important Plant Species," Plant Molecular Biology Reporter 9(3):208-218, 1991.

Rijk Zwaan Variety Convenience Catalogue, Feb. 2013.

Variety Description regarding SPN494 (Pigeon), dated Feb. 25, 2011.

Variety Description regarding SPN496 (Racoon), dated Sep. 27, 2010.

Lettuce & Spinach Terranova Seeds, Nov. 2012.

\* cited by examiner

FIG. 2

```
SDA00543_S.oleracea     1-GCAAATAGAAGTGAAATAGC:GAATATATATT::::::::::::::::::-50
SDA00543_S.tetrandra    1-GCAAATAGATGTCAAATAACTTTTTACATA:TGCAAATATATTGGAAATA-50

SDA00543_S.oleracea     51-::::::::::ATATAATATGGTTTACATAGATTTCGACAGAGGGGTTAC-100
SDA00543_S.tetrandra    51-GCGAATTATATATATAATATGGTTTACATAGCTTTCGACAGRGGGCTTAC-100

SDA00543_S.oleracea     101-TCGTATTTGTTTGAATAATATTTCATATTTGATGAAAAATAGGGATTACT-150
SDA00543_S.tetrandra    101-TCGTATTTATTTGAATAATATGTCATATTTGACG:AGAATAAGAATGACT-150

SDA00419_S.oleracea     1-GCTGCTGCATCATAGGGTAATAGTTCCTTCCTTTTTCCTTTATCATTGGT-50
SDA00419_S.tetrandra    1-GCTGCTGCATCATAGGGTGATAGTTCCTTCCTTTTTCCTTTATCATTGGT-50

SDA00419_S.oleracea     51-AGATCTTTTGGCAAAAGCCTGTATGGCACCAATACAACAAAAGGTTAAGA-100
SDA00419_S.tetrandra    51-AGATCGTTTGGCAAAAGCCTG::TGGCACCAATACAACAAAAGGTTAAGA-100

SDA00419_S.oleracea     101-TAAATTTGTTTGCTATGACCATATTCTAATCAAAAGAACATAGCAACATA-150
SDA00419_S.tetrandra    101-TAAATTTGTTTGCTATGACCATATTCTAATCAAAAGAACATAGCAACATA-150
```

METHODS AND COMPOSITIONS FOR *PERONOSPORA* RESISTANCE IN SPINACH

CROSS REFERENCE TO RELATED APPLICATIONS

This application is a continuation of co-pending U.S. application Ser. No. 15/349,677, filed Nov. 11, 2016, which is a continuation of U.S. application Ser. No. 14/509,215, filed Oct. 8, 2014, now U.S. Pat. No. 10,039,258, which claims the benefit of U.S. Provisional Application No. 61/888,501, filed Oct. 8, 2013, and U.S. Provisional Application No. 61/889,780, filed Nov. 4, 2013, each herein incorporated by reference in their entireties.

FIELD OF THE INVENTION

The present invention relates to the field of plant breeding and, more specifically, to methods and compositions for producing spinach plants with desired resistance to downy mildew.

INCORPORATION OF SEQUENCE LISTING

The sequence listing that is contained in the file named "SEMB013US_ST25.txt," which is 1.42 kilobytes as measured in Microsoft Windows operating system and was created on Oct. 7, 2014, is filed electronically herewith and incorporated herein by reference.

BACKGROUND OF THE INVENTION

Plant disease resistance is an important trait in plant breeding, particularly for production of food crops. Downy mildew, caused by the plant fungal pathogen *Peronospora farinosa* f. sp. *spinaciae*, is an economically important disease of spinach worldwide, particularly for *Spinacia oleracea*, the most commonly cultivated spinach variety. Currently, fourteen races of the Downy Mildew (DM) causing pathogen are officially recognized, although new isolates are currently being discovered and named each year. To date, it has been believed that resistance to DM in spinach was race-specific. The ability of new strains of the pathogen to overcome resistance in spinach plants thus makes the development of spinach varieties with effective levels of resistance to *Peronospora farinosa* f. sp. *spinaciae* challenging and increasingly important.

SUMMARY OF THE INVENTION

In one aspect, the invention provides a *Spinacia oleracea* spinach plant comprising in its genome an introgressed locus from *Spinacia tetrandra* that confers broad-spectrum resistance to *Peronospora farinosa* f sp. *Spinaciae*. In embodiment, the broad-spectrum resistance comprises resistance to races 7, 10, 11, 12, 13, and 14 of *Peronospora farinosa* f sp. *spinaciae* (Pfs), or to races 1-14 and UA4712 of *Peronospora farinosa* f sp. *spinaciae* (Pfs). In other embodiments, the spinach plant is defined as an inbred plant, or a hybrid plant, or an agronomically elite plant. In another embodiment, the introgressed locus is defined as flanked in the *Spinacia tetrandra* genome by sequences at least 95% identical to SEQ ID NOs:1 or 2. In yet another embodiment, a representative sample of seed comprising said locus has been deposited under Accession No. PTA-120533 or Accession No. PTA-120534. In other embodiments, the invention provides a seed that produces a *Spinacia oleracea* spinach plant comprising in its genome an introgressed locus from *Spinacia tetrandra* that confers broad-spectrum resistance to *Peronospora farinosa* f sp. *Spinaciae* or a plant part of such a plant. In still another embodiment, the plant part is selected from the group consisting of an embryo, meristem, cotyledon, pollen, leaf, anther, root, pistil, flower, cell, and stalk. In another embodiment, the invention provides a food product comprising the harvested leaves of the spinach plant comprising in its genome an introgressed locus from *Spinacia tetrandra* that confers broad-spectrum resistance to *Peronospora farinosa* f sp. *Spinaciae*.

In another aspect, the invention provides a recombined chromosomal segment comprising an allele from *Spinacia tetrandra* conferring broad-spectrum resistance to *Peronospora farinosa* f sp. *spinaciae* and lacking all or some genetic loci that are genetically linked thereto in *Spinacia tetrandra*. In one embodiment, the chromosomal segment is further defined as comprising at least a first genetic locus from *Spinacia oleracea*. In another embodiment, a representative sample of seed comprising said allele from *Spinacia tetrandra* conferring broad-spectrum resistance to *Peronospora farinosa* f sp. *spinaciae* has been deposited under Accession No. PTA-120533 or Accession No. PTA-120534. Other embodiments of the invention provide a *Spinacia oleracea* spinach plant or spinach seed comprising a chromosomal segment wherein a representative sample of seed comprising said allele from *Spinacia tetrandra* conferring broad-spectrum resistance to *Peronospora farinosa* f sp. *spinaciae* has been deposited under Accession No. PTA-120533 or Accession No. PTA-120534.

In another aspect, the invention provides a method of selecting a plant with broad-spectrum resistance to *Peronospora farinosa* f. sp. *spinaciae* comprising selecting said plant based on the presence in the genome of the plant of at least a first genetic polymorphism in or in genetic linkage disequilibrium with a chromosomal segment from *Spinacia tetrandra* conferring said resistance, wherein the locus is flanked in the *Spinacia tetrandra* genome by loci corresponding to SEQ ID NOs:1 or 2, or sequences at least 95% identical thereto. In an embodiment, the plant is a *Spinacia oleracea* plant comprising in its genome at least one introgressed locus from *Spinacia tetrandra*. In another embodiment, the plant is a *Spinacia tetrandra* plant. In yet another embodiment, the method further comprising the step of confirming the presence of said broad-spectrum resistance with a phenotypic assay. In still another embodiment, the method further comprises crossing said plant comprising the locus with another spinach plant to produce a progeny plant comprising said locus.

In another aspect, the invention provides a method for producing an agronomically elite spinach plant that comprises in its genome at least one locus conferring broad-spectrum resistance to *Peronospora farinosa* f. sp. *spinaciae* (Pfs), the method comprising: (i) crossing a first spinach plant with a second spinach plant, wherein the first plant comprises in its genome at least one locus from *Spinacia tetrandra* that confers broad-spectrum resistance to *Peronospora farinosa* f. sp. *Spinaciae*, and wherein the second plant lacks said locus; and (ii) selecting at least a first progeny spinach plant resulting from said crossing that comprises said locus. In another embodiment, the method further comprises the step of: (iii) crossing the progeny plant spinach plant with itself or another spinach plant to produce a progeny spinach plant of a subsequent generation. In another embodiment, steps (ii) and (iii) are repeated at least about 3 times to about 10 times. In still another embodiment, the first plant is a *Spinacia tetrandra* plant and the second plant is a *Spinacia oleracea* plant. In still another embodiment, selecting comprises identifying said locus in the genome of the progeny based on the detection of a genetic polymorphism as set forth in SEQ ID NOs:1 and 2 or in genetic linkage disequilibrium with said locus, wherein the locus is flanked in the *Spinacia tetrandra* genome by loci corresponding to SEQ ID NOs:1 or 2, or sequences at least 95% identical thereto.

Another aspect of the invention provides a method of producing an agronomically elite spinach plant comprising broad-spectrum resistance to *Peronospora farinosa* f. sp. *spinaciae* (Pfs), comprising introgressing into an agronomically elite *Spinacia oleracea* plant a chromosomal segment from *Spinacia tetrandra* that confers the resistance, wherein said locus is defined as located in a region of the *Spinacia tetrandra* genome flanked by loci corresponding to the *Spinacia tetrandra* allele in SEQ ID NOs:1 or 2, or sequences at least 95% identical thereto. In one embodiment, said introgressing comprises recovering essentially all of the *Spinacia oleracea* genome in said plant other than said locus by at least about 3-10 generations of backcrossing using a *Spinacia oleracea* plant as a recurrent parent. In another embodiment, the method further comprises the step of confirming the presence of said broad-spectrum resistance by a phenotypic assay. In another embodiment, the method further comprises identifying at least a first plant comprising said locus, and crossing the plant comprising said locus to another spinach plant to produce a progeny plant comprising said locus.

In another aspect, the invention provides a spinach plant or progeny thereof obtainable by introgressing a locus from *S. tetrandra* conferring broad-spectrum resistance to *Peronospora farinosa* f. sp. *spinaciae* (Pfs) into *S. oleracea*. In one embodiment, broad-spectrum resistance comprises resistance to at least races 7, 10, 11, 12, 13, and 14 of *Peronospora farinosa* f. sp. *spinaciae* (Pfs), or comprises resistance to all known races of *Peronospora farinosa* f. sp. *spinaciae* (Pfs). In other embodiments, the spinach plant is defined as an inbred plant, or a hybrid plant, or an agronomically elite plant. In another embodiment, the introgressed locus is defined as flanked by SEQ ID NOs:1 or 2 in the *Spinacia tetrandra* genome. In other embodiments, the invention provides a seed that produces a spinach plant or progeny thereof obtainable by introgressing a locus from *S. tetrandra* conferring broad-spectrum resistance to *Peronospora farinosa* f. sp. *spinaciae* (Pfs) into *S. oleracea* or a plant part of such a plant. In still another embodiment, the plant part is selected from the group consisting of an embryo, meristem, cotyledon, pollen, leaf, anther, root, pistil, flower, cell, and stalk.

BRIEF DESCRIPTION OF THE DRAWINGS

FIG. 2: Shows sequence alignments of fragments SDA00543 from *S. tetrandra* (SEQ ID NO:1) and *S. oleracea* (SEQ ID NO:3) and SDA00419 from *S. tetrandra* (SEQ ID NO:2) and *S. oleracea* (SEQ ID NO:4), which represent flanking regions of a QTL for resistance to DM from *S. tetrandra* and polymorphic nucleotides between the *S. oleracea* and *S. tetrandra* alleles.

BRIEF DESCRIPTION OF THE SEQUENCE LISTING

Figure 1:
FIG. 1: Shows two accessions (GB1860 and GB1861) of *Spinacia tetrandra* that were infected with *Peronospora farinosa* f. sp. *spinaciae* race Pfs12 and found to be uniformly resistant.

SEQ ID NO:1—Sequence of fragment SDA00543 from *Spinacia tetrandra*, representing a flanking region of a QTL for resistance to DM from *S. tetrandra*.

SEQ ID NO:2—Sequence of fragment SDA00419 from *Spinacia tetrandra*, representing a flanking region of a QTL for resistance to DM from *S. tetrandra*.

SEQ ID NO:3—Sequence of fragment SDA00543 from *Spinacia oleracea*, representing a flanking region of a QTL for resistance to DM from *S. tetrandra*.

SEQ ID NO:4—Sequence of fragment SDA00419 from *Spinacia oleracea*, representing a flanking region of a QTL for resistance to DM from *S. tetrandra*.

DETAILED DESCRIPTION OF THE INVENTION

The present invention provides methods and compositions for development of spinach varieties with resistance to downy mildew (DM) disease. The invention represents a significant advance by providing spinach plants and methods for their production comprising, for the first time, a locus conferring broad-spectrum resistance to DM. In particular, the invention provides a locus from *S. tetrandra* that confers broad spectrum resistance to DM. This locus can be introgressed into cultivated spinach plants, *S. oleracea*, and will provide resistance to DM. The introgressed region from *S. tetrandra* can be obtained from GB1860, GB1861 or any other *S. tetrandra* accessions. In accordance with the invention, the introgressed locus allele may be newly introgressed into any desired genomic background of a specific spinach variety or cultivar. For example, as set forth below, a spinach plant exhibiting resistance to DM can be crossed with a spinach plant that is not resistant to DM to produce a hybrid plant that comprises the genetic locus conferring resistance to DM. Such a hybrid may further be crossed to other spinach plants and selections carried out according to the invention to obtain new DM-resistant varieties of any desired genetic background.

Although alleles conferring resistance to certain races of DM have previously been identified in spinach, such alleles have only conferred resistance to a subset of races of *Peronospora farinosa*. In addition, the resistance alleles have typically been identified in cultivated spinach (*Spinacia oleracea*) or the wild spinach relative *Spinacia turkestanica*, which is more similar to cultivated spinach.

The present invention provides a genetic locus that confers DM resistance and is obtained from the wild spinach relative *S. tetrandra*. *S. tetrandra* is not traditionally viewed as having traits appropriate for agriculture, as it exhibits traits rendering it difficult to work with, such as seed dormancy issues. Surprisingly, the applicants found that the locus conferred high resistance to any race of *Peronospora farinosa* f. sp. *spinaciae* (Pfs). These results were surprising and unexpected. Previous reports had found that *S. tetrandra* did not have resistance to *P. farinosa* race 4 (Brandenberger et al., *HortScience* 27(20):1118-1119, 1992) and that *S. tetrandra* was resistant to race 3 alone (Eenink et al., *Zaadbelangen,* 1976). Brandenberger et al. evaluated 707 spinach accessions, including two *S. tetrandra* accessions, for resistance to *P. farinosa* race 4. It was found that only one *S. turkestanica* and one *S. oleracea* accession appeared to carry a high level of resistance, and not a single *S. tetrandra* entry.

Furthermore, the applicants found that the resistance allele from *S. tetrandra* is heritable and can be successfully introgressed into *S. oleracea*. The present invention thus represents a significant advantage by providing new alleles from *S. tetrandra*, a non-cultivated spinach species, which can be introgressed into cultivated spinach to produce spinach plants with broad-spectrum DM resistance coupled with elite agronomic traits. One aspect of the invention therefore provides a recombined chromosomal segment or "reduced introgression" comprising a locus from *S. tetrandra* providing broad-spectrum resistance to DM but lacking loci that are genetically linked thereto in *S. tetrandra*, as well as methods for the production thereof. The loci from *S. tetrandra* lacking from the chromosomal segment may in specific embodiments be associated with less desirable agronomic properties, and may be replaced with loci from *S. oleracea*, for example, to provide broad-spectrum DM resistance in combination with elite agronomic traits. In one embodiment of the invention, the genetic locus from *S. tetrandra* providing broad-spectrum resistance to DM in such a chromosomal segment comprises a region from *S. tetrandra* flanked by loci corresponding to SDA00543 (SEQ ID NO:1) and SDA00419 (SEQ ID NO:2). In further embodiments, the chromosomal segment is defined as lacking some or all genetic loci from *S. tetrandra* found outside of said region in wild type *S. tetrandra*. In still further embodiments, the genetic locus from *S. tetrandra* providing broad-spectrum resistance to DM may be from a genetic source selected from accession GB1860 and GB1861, representative deposits of seed of which were made with under Accession No. PTA-120533 and Accession No. PTA-120534, respectively.

In accordance with the invention, methods are provided for detecting a locus comprising an allele that confers broad-spectrum resistance to DM. In one embodiment, genetic markers that include, but are not limited to, the single nucleotide polymorphisms (SNPs) and insertion/deletions (INDELs), in sequence alignments SDA00543 (SEQ ID NOs:1 and 3) and SDA00419 (SEQ ID NOs:2 and 4), are provided flanking the resistance locus. FIG. 2 shows the sequence alignments described herein. Other such markers for use with the invention are also described herein. The invention therefore provides methods of identifying and selecting a spinach plant comprising in its genome a genotype conferring a desired resistance to DM that originates from a genetic locus from *S. tetrandra* and that may be introgressed into an *S. oleracea* genetic background to produce an agronomically elite inbred or hybrid variety exhibiting broad-spectrum DM resistance. The spinach plants and parts thereof made by any such methods therefore form part of the invention, as do nucleic acid sequences that may be used in the identification of polymorphisms genetically linked in a spinach genome to the DM-resistance conferring locus. The invention also provides food products derived from such plants and their method of production.

By providing genetic markers in linkage disequilibrium with DM-resistance alleles from *S. tetrandra*, the invention permits the efficient introduction of the resulting DM-resistance trait into essentially any spinach genome. This also results in significant economization by permitting substitution of costly, time-intensive, and potentially unreliable phenotypic assays. Further, breeding programs can be designed to explicitly drive the frequency of specific favorable phenotypes by targeting particular genotypes. Fidelity of these associations may be monitored continuously to ensure maintained predictive ability and, thus, informed breeding decisions.

In accordance with the invention, one of skill in the art may identify a candidate germplasm source possessing a desirable DM-resistant phenotype as described herein, such as from a given *S. tetrandra* accession. As *S. tetrandra* is a wild species, accessions can be collected from regions in which it is normally found, such as in Central Asia, including Uzbekistan and Tajikistan. In addition, accessions of *S. tetrandra* are available from genebanks including Centre for Genetic Resources, the Netherlands (CGN), Wageningen, the Netherlands and the National Plant Germplasm System of the US Department of Agriculture (USDA). A collection trip for *S. tetrandra* was undertaken in 2011 by CGN and increased the total global accessions of *S. tetrandra* to 59 (see, for example, Kik et al., 2011, The CGN Spinach Collection: Overview and Recent Collecting Expeditions (available at spinach.uark.edu/Session %20II%20PDFs/ Chirs%20Kik.pdf). One embodiment of the invention comprises using the materials and methods of the invention to obtain a locus conferring broad-spectrum resistance to DM from any additional accessions of *S. tetrandra*. Using the information set forth herein, including, but not limited to the polymorphic markers provided herein, the DM resistance from *S. tetrandra* can be introgressed into *S. oleracea* varieties without the poor agronomic properties otherwise associated with *S. tetrandra*.

The techniques of the present invention may be used to identify desirable disease-resistant phenotypes by identifying genetic markers genetically linked to an allele conferring such a phenotype. In accordance with the invention, one of skill in the art may develop molecular marker assays based on the SNPs and or INDELs that become apparent by aligning the *S. oleracea* and *S. tetrandra* alleles, for example those shown in SEQ ID NOs:1-4. In an embodiment, molecular marker assays useful to identify DM-resistant spinach plants according to the invention may be designed based on SEQ ID NOs:1 and 2. Such techniques may also involve phenotypic assays to identify desired plants either alone or in combination with genetic assays, thereby also identifying a marker genotype associated with the trait that may be used for production of new varieties with the methods described herein.

The invention provides for the introgression of at least a first locus from *S. tetrandra* conferring resistance to DM into a given genetic background. Successful spinach production depends on attention to various horticultural practices. These include soil management with special attention to proper fertilization, crop establishment with appropriate spacing, weed control, and the introduction of bees or other insects for pollination, irrigation, and pest management.

Spinach crops can be established from seed or from transplants. Transplanting can result in an earlier crop compared to a crop produced from direct seeding. Transplanting helps achieve complete plant stands rapidly, especially where higher seed costs, as with triploid seeds, make direct-seeding risky.

Development of Spinach Plants with Resistance to Downy Mildew

The present disclosure identifies loci from *S. tetrandra* conferring broad-spectrum resistance to DM, as well as markers genetically linked to and predictive of such loci that can be used for the tracking and introgression of the loci into desirable germplasm, such as by marker-assisted selection and/or marker-assisted backcrossing.

The invention thus contemplates the tracking and introduction of any such QTL and any combination with other resistance loci into a given genetic background. One of ordinary skill will understand that resistance to DM conferred by the QTL may be introgressed from one genotype to another using the primary locus described herein via marker-assisted selection. Accordingly, a germplasm source can be selected that has resistance to DM. Using this QTL, a breeder may select a spinach plant with resistance to DM, or track such phenotype during breeding using marker-assisted selection for the region described herein.

For most breeding objectives, commercial breeders may work within germplasm that is often referred to as the "cultivated type" or "elite." This germplasm is easier to use in plant breeding because it generally performs well when evaluated for horticultural performance. The performance advantage a cultivated type provides is sometimes offset by a lack of allelic diversity. This is the tradeoff a breeder accepts when working with cultivated germplasm—better overall performance, but a lack of allelic diversity. Breeders generally accept this tradeoff because progress is faster when working with cultivated material than when breeding with genetically diverse sources.

In contrast, when a breeder makes either intra-specific or inter-specific crosses, a converse trade off occurs. In these examples, a breeder typically crosses cultivated germplasm with a non-cultivated type. In such crosses, the breeder may gain access to novel alleles from the non-cultivated type, but may have to overcome the genetic drag associated with the donor parent. Because of the difficulty with this breeding strategy, this approach often fails because of fertility and fecundity problems. The difficulty with this breeding approach extends to many crops, and is exemplified with an important disease-resistant phenotype that was first described in tomato in 1944 (Smith, *Proc. Am. Soc. Hort. Sci.* 44:413-16). In this cross, a nematode disease resistance was transferred from *L. peruvianum* (PII28657) into a cultivated tomato. Despite intensive breeding, it was not until the mid-1970's before breeders could overcome the genetic drag and release successful lines carrying this trait. Indeed, even today, tomato breeders deliver this disease resistance gene to a hybrid variety from only one parent.

The process of introgressing a novel resistance gene into acceptable commercial types is a long and often arduous process and can be complicated by factors such as linkage drag, epistasis, and low heritability. The heritability of a trait is the proportion of the phenotypic variation attributed to the genetic variance, which varies between 0 and 1.0. Thus, a trait with heritability near 1.0 is not greatly affected by the environment. Those skilled in the art recognize the importance of creating commercial lines with high heritability horticultural traits because these cultivars will allow growers to produce a crop with uniform market specifications.

Genomic Region, QTL, Polymorphic Nucleic Acids, and Alleles Associated with DM Resistance Applicants have discovered a genetic locus from *S. tetrandra* that, when present, confers broad-spectrum resistance of spinach plants to DM. Using the methods outlined herein, the QTL was located in a region of *S. tetrandra* corresponding to Linkage Group 6 (LG6) of *S. oleracea*, in a locus defined by flanking sequences SDA00543 (SEQ ID NO:1) and SDA00419 (SEQ ID NO:2), or sequences at least 95% identical thereto, including sequences at least 96%, 97%, 98%, 99%, or 100% identical thereto, as one of skill in the art would understand that polymorphisms may exist in such regions in different populations. One of skill in the art will further appreciate that many genetic markers can be located throughout the *S. oleracea* genome and markers may be developed from SNPs and/or INDELs in the flanking sequences SDA00543 (SEQ ID NOs:1 and 3) and SDA00419 (SEQ ID NOs:2 and 4) and in other fragments located throughout the *S. oleracea* genome and can be used for identifying the presence or absence of a *S. tetrandra* introgression in accordance with the invention. Examples of markers are described in, for example, Khattak et al. (*Euphytica* 148:311-318, 2006). The identification of the locus and DM-resistance conferring alleles set forth herein, allows the use of any other such markers in the same region and genetically linked (in linkage disequilibrium) therewith. Examples of such other markers that may be used therefore include, but are not limited to, Dm-1 (*Phytopathology* 98:894-900, 2008). Dm-1 is a co-dominant sequence characterized amplified region (SCAR) marker linked to Pfs-1 that was predictive for resistance to race 6 and was derived from an amplified fragment length polymorphism (AFLP).

The genomic region, QTL, and polymorphic markers identified herein can be mapped relative to any publicly available physical or genetic map to place the region described herein on such map. One of skill in the art would also understand that additional polymorphic nucleic acids that are genetically linked to the QTL associated with resistance to DM in spinach and that map within about 40 cM, 20 cM, 10 cM, 5 cM, or 1 cM of the QTL or the markers associated with resistance to DM in spinach may also be used.

The above markers and allelic states are therefore exemplary. One of skill in the art would recognize how to identify spinach plants with other polymorphic nucleic acid markers and allelic states thereof related to resistance to DM in spinach consistent with the present disclosure. One of skill the art would also know how to identify the allelic state of other polymorphic nucleic acid markers located in the genomic region(s) or linked to the QTL or other markers identified herein, to determine their association with resistance to DM in spinach.

Introgression of a Genomic Locus Associated with Resistance to DM in Spinach

Provided herein are spinach plants (*S. oleracea*) comprising an introgressed genomic region from *S. tetrandra* that confers broad-spectrum resistance to DM and methods of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic region from a first germplasm (e.g., germplasm with resistance to DM) and both linked and unlinked markers characteristic of the desired genetic background of a second germplasm.

Markers that are linked and either immediately adjacent or adjacent to the identified DM-resistance QTL that permit introgression of the QTL in the absence of extraneous linked DNA from the source germplasm containing the QTL are provided herewith. Those of skill in the art will appreciate that when seeking to introgress a smaller genomic region comprising a QTL associated with resistance to DM described herein, that any of the telomere proximal or centromere proximal markers that are immediately adjacent to a larger genomic region comprising the QTL can be used to introgress that smaller genomic region.

Spinach plants or germplasm comprising an introgressed region that is associated with resistance to DM wherein at least 10%, 25%, 50%, 75%, 90%, or 99% of the remaining genomic sequences carry markers characteristic of plant or germplasm that otherwise or ordinarily comprise a genomic region associated with another phenotype, are thus provided in specific embodiments. Furthermore, spinach plants comprising an introgressed region where closely linked regions adjacent and/or immediately adjacent to the genomic regions, QTL, and markers provided herewith that comprise genomic sequences carrying markers characteristic of spinach plants or germplasm that otherwise or ordinarily comprise a genomic region associated with the phenotype are also provided.

Molecular Assisted Breeding Techniques

Genetic markers that can be used in the practice of the present invention include, but are not limited to, Restriction Fragment Length Polymorphisms (RFLP), Amplified Fragment Length Polymorphisms (AFLP), Simple Sequence Repeats (SSR), simple sequence length polymorphisms (SSLPs), Single Nucleotide Polymorphisms (SNP), Insertion/Deletion Polymorphisms (Indels), Variable Number Tandem Repeats (VNTR), Random Amplified Polymorphic DNA (RAPD), isozymes, and others known to those skilled in the art. Marker discovery and development in crops provides the initial framework for applications to marker-assisted breeding activities (U.S. Patent Pub. Nos.: 2005/0204780; 2005/0216545; 2005/0218305; and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single-strand conformational polymorphism (Orita et al. *Genomics*, 8(2):271-278, 1989), denaturing gradient gel electrophoresis (Myers EPO 0273085, 1985), or cleavage fragment length polymorphisms (Life Technologies, Inc., Gathersberg, Md. 20877), but the widespread availability of DNA sequencing machines often makes it easier to just sequence amplified products directly. Once the polymorphic sequence difference is known, rapid assays can be designed for progeny testing, typically involving some version of PCR amplification of specific alleles (PASA, Sommer et al., *Biotechniques* 12(1):82-87, 1992), or PCR amplification of multiple specific alleles (PAMSA, Dutton et al., *Biotechniques* 11(6):700-702, 1991).

As a set, polymorphic markers serve as a useful tool for fingerprinting plants to inform the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a spinach plant a genotype associated with resistance to DM, identify a spinach plant with a genotype associated with resistance to DM, and to select a spinach plant with a genotype associated with resistance to DM. In certain embodiments of methods of the invention, polymorphic nucleic acids can be used to produce a spinach plant that comprises in its genome an introgressed locus associated with resistance to DM. In certain embodiments of the invention, polymorphic nucleic acids can be used to breed progeny spinach plants comprising a locus associated with resistance to DM.

Certain genetic markers may include "dominant" or "codominant" markers. "Codominant" markers reveal the presence of two or more alleles (two per diploid individual). "Dominant" markers reveal the presence of only a single allele. Markers are preferably inherited in a codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with a DM resistance phenotype.

As used herein, nucleic acid analysis methods include, but are not limited to, PCR-based detection methods (for example, TaqMan assays), microarray methods, mass spectrometry-based methods and/or nucleic acid sequencing methods, including whole-genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. *Cold Spring Harbor Symp. Quant. Biol.* 51:263-273, 1986; European Patent No. 50,424; European Patent No. 84,796; European Patent No. 258,017; European Patent No. 237,362; European Patent No. 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613; 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981; and 7,250,252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800, 944, where sequence of interest is amplified and hybridized to probes, followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523, 2003; Cui et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group that can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer), which is designed to hybridize to the amplified DNA adjacent to the polymorphism in the presence of DNA polymerase and two differentially labeled dideoxynucleoside triphosphates. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787, in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R. F. Service *Science* 311:1544-1546, 2006.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which spinach plants can be regenerated, plant calli, plant clumps and plant cells that are intact in plants or parts of plants such as pollen, flowers, seeds, leaves, stems, and the like.

As used herein, "DM" or "downy mildew" refers to a disease of plants, such as spinach, caused by the pathogen *Peronospora farinosa* f. sp. *spinaciae*.

As used herein, "race" refers to an officially designated strain of *Peronospora farinosa* f. sp. *spinaciae* (Pfs) that can cause DM. As used herein, "isolate" refers to a newly occurring strain of *Peronospora farinosa* f. sp. *spinaciae* (Pfs) that can cause DM, and has not yet been officially named. A spinach plant with resistance to DM according to the present invention carries an introgression from *S. tetrandra* conferring DM resistance. The DM resistance may be to one or more known races of *Peronospora farinosa* f sp. *spinaciae*, or may be resistant to one or more isolates of *Peronospora farinosa* f sp. *spinaciae*. In another embodiment, a plant of the invention may be defined as resistant to at least *Peronospora farinosa* f. sp. *spinaciae* Pfs 7, 10, 11, 12, 13, and/or 14.

As used herein, the term "population" means a collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, the term "introgressed," when used in reference to a genetic locus, refers to a genetic locus that has been introduced into a new genetic background, such as through backcrossing. Introgression of a genetic locus can thus be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, the term "denoting" when used in reference to a plant genotype refers to any method whereby a plant is indicated to have a certain genotype. This includes any means of identification of a plant having a certain genotype. Indication of a certain genotype may include, but is not limited to, any entry into any type of written or electronic medium or database whereby the plant's genotype is provided. Indications of a certain genotype may also include, but are not limited to, any method where a plant is physically marked or tagged. Illustrative examples of physical marking or tags useful in the invention include, but are not limited to, a barcode, a radio-frequency identification (RFID), a label, or the like.

DEPOSIT INFORMATION

Deposits of seeds of *Spinacia tetrandra* accessions designated GB1860 and GB1861 have been maintained by Seminis Vegetable Seeds, Inc. from prior to the time of filing of this application. Deposits of at least 2500 seeds were also made with the American Type Culture Collection (ATCC). The address for the ATCC is 10801 University Boulevard, Manassas, Va. 20110-2209 USA. The deposits are assigned Accession Nos. PTA-120533 and PTA-120534. The date of deposit of these accessions was Aug. 14, 2013. Access to the deposits will be available during the pendency of the application to persons entitled thereto upon request. The deposits will be maintained in the depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

EXAMPLES

The following disclosed embodiments are merely representative of the invention which may be embodied in various forms. Thus, specific structural, functional, and procedural details disclosed in the following examples are not to be interpreted as limiting.

Example 1

Identification of Broad Spectrum Resistance to Downy Mildew in *Spinacia tetrandra*

*Spinacia tetrandra* represents a small subset of the *Spinacia* genebank collections available. Four accessions of *S. tetrandra* were included in the study. A disease test, such as the assay described in Example 2, was designed to include the four *S. tetrandra* accessions, three additional *S. turkestanica* accessions, and one accession of an unknown species, possibly *S. tetrandra*. Non-cultivated spinach accessions such as *S. tetrandra* exhibit difficult seed dormancy issues that can cause problems in plant breeding. In the present study, compared to other entries, *S. tetrandra* seeds suffered from severe lack of germination, consistent with a study by Brenner (The U.S. Spinach Germplasm Collection, paper presented at The T. E. Morelock International Spinach Conference, Fayetteville, A R, 2009), which observed from 9 *S. tetrandra* accessions that some seeds germinated in the Fall following January plantings.

Disease assays were performed with officially designated races Pfs 10, 12, and 14. In contrast to the *S. turkestanica* entries used in the study, two *S. tetrandra* accessions, designated GB1860 and GB1861, were found to carry resistance to all races tested. These results were confirmed on 20 mature plants infected with race Pfs 12, which demonstrated a uniform and clearly resistant response (FIG. 1).

The finding that *S. tetrandra* demonstrated resistance to multiple races was in contrast to earlier reports. Brandenberger and coworkers (*Hortscience*, 27(20):1118-1119, 1992) evaluated 707 spinach accessions for resistance to race 4, two of the accessions were *S. tetrandra*. Only one *S. turkestanica* and one *S. oleracea* accession appeared to carry a high level of resistance, and not a single *S. tetrandra* entry. In addition, Eenink et al. found that *S. tetrandra* was resistant to race 3 alone (Zaadbelangen, 1976).

As a next step, the two *S. tetrandra* accessions, GB1860 and GB1861, found to be resistant to all races were crossed to the elite *S. oleracea* inbred line OEB-66-1056F, and resistant F1 plants were selected. Subsequently, a backcross was performed between selected F1 plants and inbred line OEB-66-1056F. Two BC1 families were derived from one of the resistant *S. tetrandra* accessions, designated "8" and "15," respectively. These two families were tested in a disease test for resistance to DM races Pfs 7, 10, 11, 12, 13, and 14. BC1 family "8" was found to carry resistance to all races tested (Table 1). Similarly, BC1 family "15" also harbored resistance to these races, with the exception of race Pfs 10. As expected, resistance was found to segregate in the BC1 families, consistent with the heterogeneous nature of *S. tetrandra* plant introductions. Based on resistance to all officially designated races tested, the two *S. tetrandra* accessions appear to carry broad spectrum resistance to *Peronospora farinosa* f. sp. *spinaciae*. These results were surprising and in contrast to previous findings that resistance to DM in spinach is always race-specific. Furthermore, studies of BC1 families demonstrated that resistance to DM from *S. tetrandra* is heritable and can be introgressed into *S. oleracea*.

TABLE 1

Phenotypic scores of two BC1 families derived from S. tetrandra accessions

| Isolate BC1 individual | Pfs 12 | | | | | | | | Pfs 14 | | | | | | Pfs 11 | | | |
|---|---|---|---|---|---|---|---|---|---|---|---|---|---|---|---|---|---|---|
| 15-168 | 0 | 0 |   | 0 | 0 |   | 0 | 0 |   | 0 | 0 |   | 0 | 0 |   | 0 | 0 |   |
| 15-164 | 0 | 0 |   | 0 | 0 |   | 0 | 0 |   | 0 | 0 |   | 0 | 0 |   | 0 | 0 |   |
| 15-160 | 0 | 0 |   | 0 | 0 |   | 0 | 0 |   | 0 | 0 |   | 0 | 0 |   | 0 | 0 |   |
| 15-159 | 0 | 0 | 0 | 0 | 0 | 0 | 0 | 0 |   | 0 | 0 | 0 | 0 | 0 |   | 0 | 0 | 0 |
| 15-166 | 0 | 0 | 0 | 0 | 0 | 0 | 0 | 0 | 0 | 0 | 0 |   | 0 | 0 | 0 | 0 | 0 | 0 |
| 15-158 | 0 | 0 |   | 0 | 0 |   | 5 | 0 |   | 70 | 0 |   | 0 | 0 |   | 30 | 0 |   |
| 15-163 | 0 | 0 | 40 | 0 | 0 | 80 | 30 | 0 | 60 | 60 | 0 | 70 | 0 | 0 | 90 | 30 | 20 |   |
| 15-165 | 0 | 0 | 0 | 50 | 40 | 0 | 10 | 0 | 0 | 20 | 0 | 0 | 60 | 0 | 0 | 0 | 0 | 0 |
| 8-133 | 0 | 0 | 0 | 0 | 0 | 0 | 0 | 0 | 0 | 0 | 0 | 0 | 0 | 0 | 0 | 0 | 0 | 0 |
| 8-134 | 0 | 0 | 0 | 0 | 0 | 0 | 0 | 0 | 0 | 0 | 0 | 0 | 0 | 0 | 0 | 0 | 0 | 0 |
| 8-135 | 0 | 0 | 0 | 0 | 0 | 0 | 0 | 0 | 0 | 0 | 0 | 0 | 0 | 0 | 0 | 0 | 0 | 0 |
| 8-137 | 0 | 0 | 0 | 0 | 0 | 0 | 0 | 0 |   | 0 | 0 |   | 0 | 0 |   | 0 | 0 |   |
| 8-128 | 0 | 0 |   | 0 | 0 |   | 0 | 0 |   | 0 | 0 |   | 0 | 0 |   | 0 | 0 |   |
| 8-129 | 0 | 0 |   | 0 | 0 |   | 0 | 0 |   | 0 | 0 |   | 0 | 0 |   | 0 | 0 |   |
| 8-131 | 0 | 0 | 0 | 0 | 0 | 0 | 0 | 0 | 0 | 5 | 0 | 0 | 0 | 0 | 0 | 0 | 0 | 0 |
| 8-132 | 5 | 0 |   | 40 | 0 | 0 | 0 | 0 |   | 0 | 0 | 0 | 0 | 0 | 0 | 0 | 0 |   |
| 8-138 | 5 | 0 | 0 | 0 | 0 | 0 | 50 | 0 | 0 | 0 | 0 | 0 | 30 | 10 | 0 | 0 | 0 | 0 |
| 8-136 | 20 | 0 |   | 0 | 0 |   | 20 | 0 | 0 | 0 | 0 |   | 25 | 0 |   | 3 | 0 |   |
| 8-130 | 60 | 40 |   | 50 | 10 |   | 70 | 0 |   | 80 | 30 |   | 50 | 0 | 0 | 30 | 10 |   |

| Isolate BC1 individual | Pfs 13 | | | | | | Pfs 7 | | | | | | Pfs 10 | | | | | |
|---|---|---|---|---|---|---|---|---|---|---|---|---|---|---|---|---|---|---|
| 15-168 | 0 | 0 |   | 0 | 0 |   | 0 | 0 |   | 0 | 0 |   | 0 | 0 | 0 | 40 | 0 |   |
| 15-164 | 0 | 0 |   | 0 | 0 |   | 0 | 0 |   | 0 | 0 |   | 5 | 5 |   | 5 | 0 | 0 |
| 15-160 | 0 | 0 |   | 0 | 0 |   | 0 | 0 | 0 | 0 | 0 | 0 | 20 | 0 |   | 0 | 5 | 0 |
| 15-159 | 0 | 0 | 0 | 0 | 0 | 0 | 0 | 0 | 0 | 60 | 5 | 0 | 50 | 0 | 0 | 40 | 0 | 0 |
| 15-166 | 0 | 0 | 0 | 0 | 0 | 0 | 0 | 0 | 0 | 60 | 0 | 0 | 40 | 20 | 0 | 20 | 40 | 0 |
| 15-158 | 30 | 5 |   | 40 | 0 |   | 0 | 0 |   | 0 | 0 |   | 40 | 0 |   | 30 | 0 |   |
| 15-163 | 60 | 0 | 0 | 0 | 0 | 0 | 20 | 0 | 0 | 0 | 0 | 0 | 30 | 0 | 0 | 60 | 10 | 0 |
| 15-165 | 60 | 60 | 0 | 40 | 0 | 0 | 10 | 0 | 0 | 40 | 0 | 0 | 30 | 10 | 0 | 5 | 5 | 0 |
| 8-133 | 0 | 0 | 0 | 0 | 0 |   | 0 | 0 | 0 | 0 | 0 | 0 | 0 | 0 | 0 | 0 | 0 | 0 |
| 8-134 | 0 | 0 | 0 | 0 | 0 | 0 | 0 | 0 | 0 | 0 | 0 | 0 | 0 | 0 | 0 | 0 | 0 | 0 |
| 8-135 | 0 | 0 | 0 | 0 | 0 |   | 0 | 0 | 0 | 0 | 0 | 0 | 0 | 0 | 0 | 0 | 0 | 0 |
| 8-137 | 0 | 0 |   | 0 | 0 |   | 0 | 0 |   | 0 | 0 |   | 0 | 0 |   | 0 | 0 |   |
| 8-128 | 0 | 0 |   | 0 | 0 |   | 0 | 0 |   | 0 | 0 |   | 0 | 0 |   | 40 | 10 |   |
| 8-129 | 0 | 0 |   | 0 | 0 |   | 20 | 0 |   | 0 | 0 |   | 20 | 10 |   | 30 | 0 |   |
| 8-131 | 0 | 0 | 0 | 0 | 0 | 0 | 0 | 0 | 0 | 0 | 0 | 0 | 0 | 0 | 0 | 10 | 0 | 0 |
| 8-132 | 5 | 0 | 0 | 0 | 0 | 0 | 0 | 0 | 0 | 0 | 0 | 0 | 0 | 0 | 0 | 0 | 0 | 0 |
| 8-138 | 0 | 0 |   | 0 | 0 |   | 0 | 0 | 0 | 0 | 0 |   | 0 | 0 |   | 60 | 0 |   |
| 8-136 | 40 | 0 |   | 0 | 0 |   | 0 | 0 |   | 15 | 30 | 0 | 0 | 40 |   | 20 | 0 |   |
| 8-130 | 80 | 30 | 0 | 0 | 0 |   | 30 | 0 | 0 | 35 | 10 |   | 60 | 5 |   | 60 | 5 |   |

Infection level was determined relative to the susceptible control. Four to six samples of 8-10 individuals per BC1 family were infected with Pfs 7, 10, 11, 12, 13 or 14. A score of 0 indicates no infection. A score of 100 indicates complete infection; infection rates above, on average, 1% are indicated by bold and underline.

Additional BC1 families were tested in a cotyledon test for resistance to DM races Pfs 10, 11, 12, 13, and 14. Ten samples were evaluated in each family for resistance or susceptibility (R—Resistance; S—Susceptible; NT—Not Tested). BC families 38, 27 and 32 carried resistance to all races tested.

TABLE 2

Phenotypic scores of BC1 families derived from S. tetrandra accessions

| F1 Donor Population | BC1 Family | Pfs races tested | | | | |
|---|---|---|---|---|---|---|
| | | Pf10 | Pf11 | Pf12 | Pf13 | Pf14 |
| GB-1860 | 34 | NT | NT | R | NT | NT |
| GB-1860 | 36 | R | R | R | NT | NT |
| GB-1860 | 38 | R | R | R | R | R |
| GB-1860 | 27 | R | R | R | R | R |
| GB-1860 | 30 | R | R | R | NT | NT |
| GB-1860 | 32 | R | R | R | R | R |
| GB-1861 | 33 | R | R | S | NT | R |
| GB-1861 | 44 | NT | NT | S | NT | NT |
| GB-1861 | 53 | NT | NT | S | NT | NT |
| GB-1861 | 0001 | NT | NT | R | NT | NT |
| GB-1861 | 0002 | R | S | R | NT | NT |

Example 2

Assays for Screening Spinach Accessions for Resistance to Downy Mildew

The test utilized for screening spinach accessions for resistance to downy mildew originated from the International Union for the Protection of New Varieties of Plants (UPOV). The "Protocol for Tests on Distinctness, Uniformity, and Stability of *Spinacia oleracea* L. Spinach," UPOV Code: SPINA_OLE, CPVO-TP/055/5 was adopted and into force on Feb. 27, 2013. The protocol is as follows:

Races of *Peronospora farinosa* f. sp. *spinaciae* are maintained on living host plants, obtainable from Naktuinbouw (P.O. Box 40, NL-2370 AA, Roelofarendsveen, Netherlands, naktuinbouw.com), or plant material with spores stored at −20° C. for a maximum of one year.

Execution of test: Growth stage of plants: First cotyledons/leaf, eleven-day-old plants; Temperature: 15° C. during day/12° C. during night; Light: 15 hours per day, after emergence; Growing method: In soil in pots or trays in a glasshouse or growth chamber.

Method of inoculation: Sporulating leaves, taken from host plants that were infected seven days before, are thoroughly rinsed with sterile tap water (maximum 150 ml water per 224 plants). The spore suspension is filtered through cheesecloth and sprayed on test plants until the inoculum covers the leaves but does not run off 150 ml of suspension is enough for up to 3×224 plants. Spore density should be 20,000 to 100,000 conidia/ml water. The spore suspension should be used fresh. As spinach downy mildew is windborne, sporulating plants should be kept in closed containers or isolated chambers to prevent any cross-contamination.

Resistant controls are needed in each multiplication and in each test to ensure the race identity. Light and humidity conditions during seedling development and incubation are critical. Optimal humidity of approximately 80-90% RH allows plant growth and fungal growth; strong light inhibits spore germination and infection. The test should be carried out in wintertime with protection against direct sunshine. After inoculation, the plants should remain under plastic for three days. After this time, the plastic should be slightly raised during the daytime.

Duration of test: Multiplication harvest spores 7 days after inoculation; Sowing to inoculation: 11 days; Inoculation to reading: 10 days; Number of plants tested: 56 plants; Evaluation of infection: Resistance is usually complete; sometimes necrotic spots are visible as a result of infection. Susceptible plants show varying degrees of sporulation. Sporulation is visible as a grey covering on leaves, starting on the more humid abaxial side.

Differential varieties to identify races: Races Pfs: 1-8 and 10-13 of *Peronospora farinosa* f sp. *spinaciae* are defined with a standard set of "differential varieties" according to Table 3.

TABLE 3

Differential varieties to identify races: Races Pfs: 1-8 and 10-13 of *Peronospora farinosa* f. sp. *spinaciae*.

| Differential variety | Pfs: 1 | Pfs: 2 | Pfs: 3 | Pfs: 4 | Pfs: 5 | Pfs: 6 | Pfs: 7 | Pfs: 8 | Pfs: 10 | Pfs: 11 | Pfs: 12 | Pfs: 13 |
|---|---|---|---|---|---|---|---|---|---|---|---|---|
| Viroflay | S | S | S | S | S | S | S | S | S | S | S | S |
| Resistoflay | R | R | S | S | S | S | S | S | S | S | S | S |
| Califlay | R | S | R | S | R | S | S | R | S | R | R | S |
| Clermont | R | R | R | R | S | S | S | S | S | S | S | S |
| Campania | R | R | R | R | R | S | R | S | S | R | S | S |
| Boeing | R | R | R | R | R | R | R | S | S | R | S | R |
| Lion | R | R | R | R | R | R | R | R | S | R | R | R |
| Lazio | R | R | R | R | R | R | R | R | R | S | S | S |

R, resistance present;
S, resistance absent (susceptible)

Example 3

Mapping Resistance to Downy Mildew in *S. tetrandra*

In view of the disease assay and heterogeneity of *S. tetrandra*, markers associated with resistance were identified for efficient and accurate selection of favorable alleles. Resistance to DM inherited from *S. tetrandra* was mapped in a BC1 population, which was developed as described in Example 1. A total of 54 individuals were phenotyped using *Peronospora farinosa* f sp. *spinaciae* race 12. These BC1 individuals were scored in two classes, demonstrating either strong resistance or a fully susceptible response. Markers located within a narrow interval of Linkage Group 6 (LG6) that encompasses resistance in *S. oleracea* were selected for further study (Table 4) (Khattak et al., *Euphytica* 148:311-318, 2006). A mapping study was performed with mapQTL using the standard interval mapping.

A resistance locus was detected and demonstrated by statistically significant association (>LOD=3) of markers in the interval delineated by converted SSR marker sequences, for example SDA00419 (SEQ ID NOs:2 and 4), with resistance to Pfs race 12 (Table 4). The QTL appeared to have a major effect and explained approximately 65% of the observed variation. An approximation of the position of DM resistance from *S. tetrandra* was between markers E33/M62-231 at 0.0 cM and E39/M47-203 at 10.3 cM, on chromosome 6 of the public map (Khattak et al., *Euphytica* 148:311-318, 2006).

This result demonstrates that race-specific resistance to *Peronospora farinosa* f. sp. *spinaciae* in *S. oleracea* is collinear with broad spectrum resistance from *S. tetrandra*. This is surprising, as the nature and origin of both resistances is distinct.

TABLE 4

Map position, LOD scores, and locus identity of markers used in association study

| map | lod | iter | mu_H | mu_B | var | % expl | add | locus |
|---|---|---|---|---|---|---|---|---|
| 0 | 13.04 | 5 | 84.4428 | 4.45461 | 754.794 | 67.9 | 79.9882 | p23m39 |
| 3 | 11.93 | 5 | 79.3313 | 0.84541 | 833.287 | 64.6 | 78.4859 | SD100762_SNP |
| 3 | 11.93 | 5 | 79.3313 | 0.84541 | 833.287 | 64.6 | 78.4859 | SD100762_InDel |
| 3 | 11.93 | 5 | 79.3313 | 0.84541 | 833.287 | 64.6 | 78.4859 | SDA00538 |
| 3.5 | 11.92 | 5 | 79.3313 | 0.845488 | 833.29 | 64.6 | 78.4858 | SDA00419 |

Example 4

New Isolates of *Peronospora farinosa* f Sp. *Spinaciae* do not Break Resistance from *S. tetrandra*

Novel, virulent isolates of *Peronospora farinosa* f. sp. *spinaciae* arise regularly and globally. To date, 14 races have been officially named, recently at a rate of one per year. Two BC1 families, described in Example 1, were tested in a leaf disc assay with a resistance breaking strain, SE4712. SE4712 was isolated from a field in California, US, in the spring of 2013. It was subsequently re-named by the International Working Group on *Peronospora* (IWPG) as UA4712. It has been shown to break existing resistance to DM and has not yet received an official race designation.

Four to six samples of 8-10 individuals per BC1 family were infected with isolate UA4712. Infection levels were determined relative to the susceptible control. A Score of 0 indicates no infection. All individuals of both BC1 families appeared to be resistant to isolate UA4712 (Table 5). This observation is consistent with broad spectrum resistance to *Peronospora farinosa* f. sp. *spinaciae* from *S. tetrandra*.

TABLE 5

Phenotypic scores of two BC1 families derived from *S. tetrandra* accessions. A score of "0" indicates no infection.

| BC1 individual | Isolate SE4712 | | | | | |
|---|---|---|---|---|---|---|
| 15-168 | 0 | 0 | | 0 | 0 | |
| 15-164 | 0 | 0 | | 0 | 0 | |
| 15-160 | 0 | 0 | | 0 | 0 | |
| 15-159 | 0 | 0 | 0 | 0 | 0 | 0 |
| 15-166 | 0 | 0 | 0 | 0 | 0 | 0 |
| 15-158 | 0 | 0 | 0 | 0 | 0 | 0 |
| 15-163 | 0 | 0 | 0 | 0 | 0 | 0 |
| 15-165 | 0 | 0 | 0 | 0 | 0 | 0 |
| 8-133 | 0 | 0 | 0 | 0 | 0 | 0 |
| 8-134 | 0 | 0 | 0 | 0 | 0 | 0 |
| 8-135 | 0 | 0 | 0 | 0 | 0 | 0 |
| 8-137 | 0 | 0 | 0 | 0 | 0 | |
| 8-128 | 0 | 0 | 0 | 0 | 0 | 0 |
| 8-129 | 0 | 0 | | 0 | 0 | 0 |
| 8-131 | 0 | 0 | 0 | 0 | 0 | 0 |
| 8-132 | 0 | 0 | 0 | 0 | 0 | 0 |
| 8-138 | 0 | 0 | 0 | | | |
| 8-136 | 0 | 0 | | | 0 | |
| 8-130 | 0 | 0 | | 0 | 0 | |

What is claimed is:

1. A recombined chromosomal segment comprising an allele from *Spinacia tetrandra* conferring broad-spectrum resistance to *Peronospora farinosa* f. sp. *spinaciae* (Pfs) and at least a first genetic locus from *Spinacia oleracea*, wherein said allele confers broad-spectrum resistance to *Peronospora farinosa* f. sp. *spinaciae* when present in a spinach plant, wherein the broad-spectrum resistance comprises resistance to races 7, 10, 11, 12, 13, and 14 of *Peronospora farinosa* f. sp. *spinaciae* (Pfs), wherein said allele comprises sequences at least 99% identical to SEQ ID NO:1 and SEQ ID NO:2, wherein a representative sample of seed comprising said allele has been deposited under Accession No. PTA-120533 or Accession No. PTA-120534.

2. The chromosomal segment of claim 1, further defined as lacking all or some genetic loci that are genetically linked to said allele in *Spinacia tetrandra*.

3. A *Spinacia oleracea* spinach plant comprising the chromosomal segment of claim 1.

4. A *Spinacia oleracea* spinach seed comprising the chromosomal segment of claim 1.

5. A *Spinacia oleracea* spinach cell comprising the chromosomal segment of claim claim 1.

* * * * *

SEQUENCE LISTING

<160> NUMBER OF SEQ ID NOS: 4

<210> SEQ ID NO 1
<211> LENGTH: 148
<212> TYPE: DNA
<213> ORGANISM: Spinacia tetrandra

<400> SEQUENCE: 1

```
gcaaatagat gtgaaataac tttttacata tgcaaatata ttggaaatag cgaattatat    60
atataatatg gtttacatag gtttcgacag agggcttact cgtatttatt tgaataatat   120
gtcatatttg acgagaataa gaatgact                                       148
```

<210> SEQ ID NO 2
<211> LENGTH: 148
<212> TYPE: DNA
<213> ORGANISM: Spinacia tetrandra

<400> SEQUENCE: 2

```
gctgctgcat catagggtga tagttccttc cttttttcctt tatcattggt agatcgtttg    60
gcaaaagcct gtggcaccaa tacaacaaaa ggttaagata aatttgtttg ctatgaccat   120
attctaatca aaagaacata gcaacata                                       148
```

<210> SEQ ID NO 3
<211> LENGTH: 120

```
<212> TYPE: DNA
<213> ORGANISM: Spinacia oleracea

<400> SEQUENCE: 3
gcaaatagaa gtgaaatagc gaatatatat tatataatat ggtttacata gatttcgaca      60
gaggggttac tcgtatttgt ttgaataata tttcatattt gatgaaaaat agggattact     120

<210> SEQ ID NO 4
<211> LENGTH: 150
<212> TYPE: DNA
<213> ORGANISM: Spinacia oleracea

<400> SEQUENCE: 4
gctgctgcat catagggtga tagttccttc cttttttcctt tatcattggt agatcttttg     60
gcaaaagcct gtatggcacc aatacaacaa aaggttaaga taaatttgtt tgctatgacc    120
atattctaat caaaagaaca tagcaacata                                      150
```

UNITED STATES PATENT AND TRADEMARK OFFICE
CERTIFICATE OF CORRECTION

| | |
|---|---|
| PATENT NO. | : 11,134,628 B2 |
| APPLICATION NO. | : 16/680292 |
| DATED | : October 5, 2021 |
| INVENTOR(S) | : Bart Willem Brugmans et al. |

It is certified that error appears in the above-identified patent and that said Letters Patent is hereby corrected as shown below:

On the Title Page

Item (72), Line 3, delete "Rosa I. Weber" and please insert --Inge Weber--

Signed and Sealed this
Seventh Day of February, 2023

Katherine Kelly Vidal
*Director of the United States Patent and Trademark Office*